Figure 1:
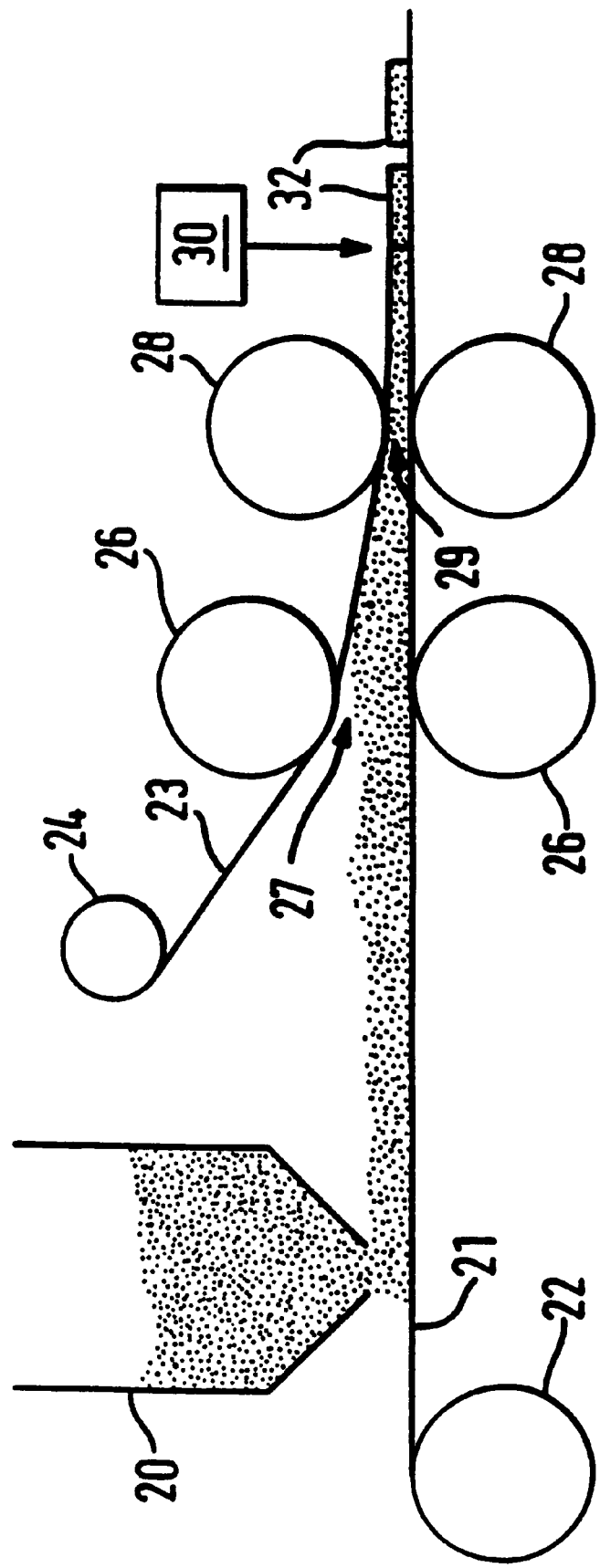
Figure 2:
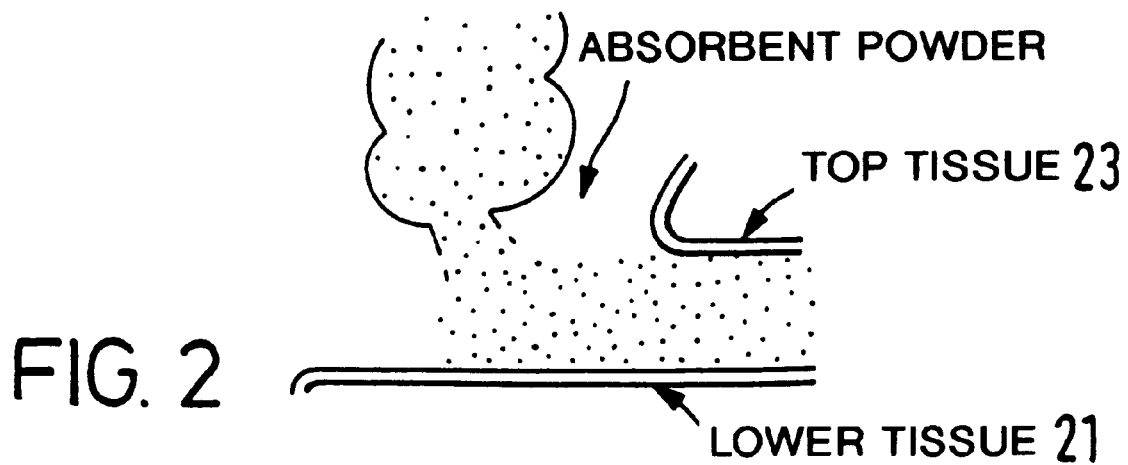
Figure 3:
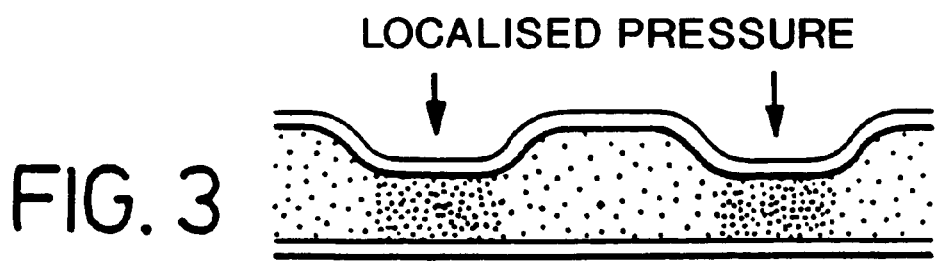
Figure 4:
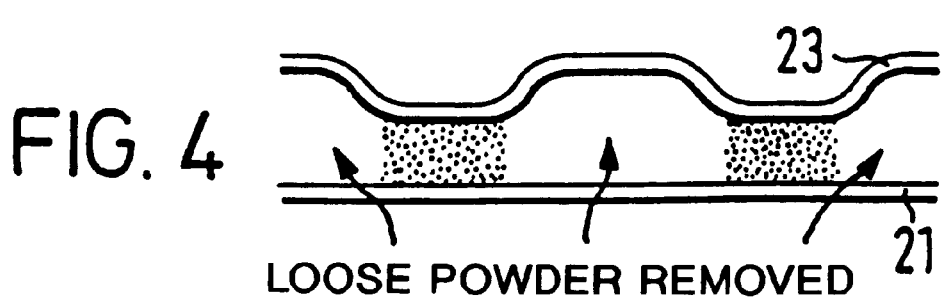

United States Patent

Gent

[11] Patent Number: 6,054,631
[45] Date of Patent: Apr. 25, 2000

[54] ABSORBING AQUEOUS MATTER

[75] Inventor: John A. Gent, Hampshire, United Kingdom

[73] Assignee: Bristol-Myers Squibb Company, New York, N.Y.

[21] Appl. No.: 09/074,716

[22] Filed: May 8, 1998

[30] Foreign Application Priority Data

May 21, 1997 [GB] United Kingdom .................... 9710473

[51] Int. Cl.[7] ............................. A61F 13/15; B32B 31/00; B31F 53/00
[52] U.S. Cl. ......................... 604/367; 604/358; 604/367; 604/378; 604/379; 604/380; 604/385.1; 604/368; 156/276; 156/219; 156/290
[58] Field of Search .................................... 156/276, 219, 156/290; 604/368, 358, 367, 378, 379, 380, 385.1

[56] References Cited

U.S. PATENT DOCUMENTS

| 4,715,918 | 12/1987 | Lang | 156/273.1 |
| 4,988,344 | 1/1991 | Reising et al. | 604/368 |
| 5,643,238 | 7/1997 | Baker | 604/368 |

Primary Examiner—John G. Weiss
Assistant Examiner—Miley Craig Peppers, III
Attorney, Agent, or Firm—Stuart E. Krieger

[57] ABSTRACT

In a method of making high-absorbency articles for use in wound care, incontinence, ostomy applications, and other more varied uses, a loose high-absorbency powder is arranged between a pair of sheets. The sheets and powder are compressed in certain areas. Loose powder is extracted e.g. by vacuum or gravity, and by cutting and sealing, packet-like articles are produced.

8 Claims, 3 Drawing Sheets

ABSORBING AQUEOUS MATTER

This invention relates to a product for absorbing aqueous matter and to a method of making such a product.

Many products and devices have been tried and used to absorb aqueous matter for various purposes, for example ostomy, incontinence, diapers, wound care, napkins including bibs for oral spillage/dribbling, horticultural, fruit and meat packaging and other purposes.

In 1970 in British Patent Specification No. 1,193,433 a sanitary aid was disclosed which comprised a fibrous cover containing as filling material a water soluble cellulose ether in fibre, powder or granular form.

U.S. Pat. No. 4,055,180 of 1977 taught that an absorbent article should include a hydrocolloid material which is retained in a fixed position within the article, in order to improve its performance. The absorbent pad assembly has an absorbent pad, and a first retaining sheet. The sheet is attached to the pad or a second retaining sheet in areas and is free of attachment in regions between the areas to define pocket means. The pad assembly has a hydrocolloid material positioned in the pocket means.

In 1981, Chemische Fabrik Stockhausen & Cie in DE-3, 002,136A disclosed an absorbent body, for use as a bandage etc., which has a supporting layer to which a liquid-absorbent layer is secured. The supporting layer is coated with swelling absorbent powder and thermoplastic material in powder form, over which is a layer of covering material. The supporting and/or covering layers can be cloths of cellular or synthetic fibre materials, typically creped.

International PCT Application No. WO 90/05513 (Mitchell et al) discloses an absorbent product for personal use which embodies a so-called superabsorbent. To produce the product, a laminated assembly is subjected to embossing.

UK published Application No. 2,049,553A discloses a water-absorbent sheet assembly which comprises two sheets at least one of which is a water-permeable sheet, and a polymeric absorbent inserted between said two sheets. Parts of the two sheets have been bonded together by pressing. Apparatus for preparing such a sheet includes a smooth roll and an embossing roll having convexities, concavities, and flat portions.

U.S. Pat. No. 5,030,314 relates to an article including particles which are of superabsorbent material. These are disposed between a permeable cover layer and a composite web containing discrete areas of superabsorbent material. Hence there is formed an absorbent structure such as a diaper, incontinent garment or feminine pad. In the manufacture of such a composite web, a roll is used having cavities suitable for retaining small quantities of superabsorbent. By rotating the roll, these quantities are deposited on the web, which has an impermeable backing. The permeable cover layer is joined to the web by lines of adhesive.

U.S. Pat. No. 5,118,376 is concerned with the incorporation of superabsorbent material in the fibre padding of disposable hygiene articles. A procedure used consists in compressing locally the fibre padding by means of a profiled tool, and in placing the powdery product in the impression left by the tool. According to an additional characteristic of the procedure, a compression force is then applied on the product in order to set it in the fibrous mass.

In PCT Application NO. WO 95/03019 there is disclosed a process and apparatus for manufacturing a continuous web-like intermediate absorbent product comprising an absorbent material in powder, granule or fibre form, placed between containing sheets. Such a process comprises the steps of:

a. depositing onto a web-like supporting sheet fed from a feeding reel, a predetermined pattern of absorbent material in powder, granule or fibre form;
b. bonding, by means of heat, said deposited absorbent material to the supporting sheet;
c. depositing longitudinal strips of an adhesive material onto said web-like sheet;
d. applying at least a further web-like sheet over the assembly and joining said further sheet to the former sheet in the region of said adhesive strips by compression;
e. if required, carrying out one or more times the steps from a. to d. using a latest applied web-like sheet as supporting sheet;
f. longitudinally slitting the web-like composite assembly so obtained, and
g. separately winding into rolls the narrower webs so obtained which comprise adjacent absorbent cores.

U.S. Pat. No. 5,494,622 relates to forming a composite web having selected discrete pocket regions which are distributed on a carrier layer and contain high-absorbency material. The invention includes a pattern chamber having opposed side walls, an entrance end wall and an exit end wall. A particulate supplying mechanism provides particles of high-absorbency material into the pattern chamber, and a web supplying mechanism provides a gas permeable carrier layer. A foraminous forming mechanism moves the carrier layer through the pattern chamber, and the forming mechanism includes a pattern of openings which are formed therethrough and are arranged to provide for a selected pattern of the discrete pocket regions. A vacuum supplying mechanism provides a selected level of relatively low gas pressure at an underside region of the forming mechanism to produce a selected gas-flow through the carrier layer and the foraminous forming mechanism to form the pocket regions. A covering mechanism provides a layer of liquid-permeable covering material to sandwich said pocket regions of high-absorbency material between said carrier layer and said covering layer. The aim of the inventors is to achieve a zoned placement of superabsorbent material within a composite web. Though this patent discloses the application of vacuum to provide gas flow through a layer, in order to form pocket regions, it is not concerned with compressing the composite web only in selected areas prior to removal of loose superabsorbent powder.

According to one aspect of the present invention, there is provided a method of making articles capable of absorbing aqueous matter comprising:
 a. arranging loose high-absorbent powder (preferably a "superabsorbent" powder) generally uniformly between upper and lower sheets;
 b. compressing the powder and sheets in specific areas (not over the entire area of the sheet), so as to structurally consolidate the powder in the compressed areas, while the powder in the surrounding areas remains loose; and
 c. extracting the loose powder.

Preferably the method further comprises cutting and/or sealing the regions around the consolidated areas, for example, to form individual packet-like articles or a strip of such articles.

According to another aspect of the invention, there is provided a packet-like article which comprises a compressed high-absorbent powder disposed between upper and lower layers, the layers being sealed to each other around the periphery of the article.

Preferred and advantageous features of the invention will now be discussed. In UK Patent Application No. 2,301,350 there is described a continuous roll or sheet preparation method which necessitates cutting the superabsorbent pad to the desired size for the end application. The cutting operation leads to a certain amount of shedding of formulated superabsorbent particles, and depending upon size of superabsorbent product required, the cutting operation may lead to significant percentages of scrap. Clearly it would be desirable to avoid wastage since superabsorbents are relatively expensive materials.

In the making of sealed packet-like articles in accordance with an embodiment of the invention, the superabsorbent powder is metered onto a suitable web, e.g. a web of paper tissue, by the use of a doctor blade to provide a desired weight per unit area thereon. A second web, which may but need not be paper tissue, is then placed over the powder on the first web. The resulting laminate is subjected to pressure at the nip of a pair of specially designed rollers. These rollers are constructed that pressure is applied only at chosen regularly-spaced zones. In these zones, the first and second webs and the powder therebetween are compacted, but in the remaining areas no compaction occurs and the powder remains loose and powdery. This loose powder is removed, either by vacuum suction or by gravity. Removal by gravity may be achieved by causing the laminated and intermittently-compressed webs to adopt a vertical or near-vertical planar position, whereupon the loose powder falls out and is collected for re-use. Alternatively, removal of the loose powder by suction can be achieved in a conventional manner.

Figure 5:
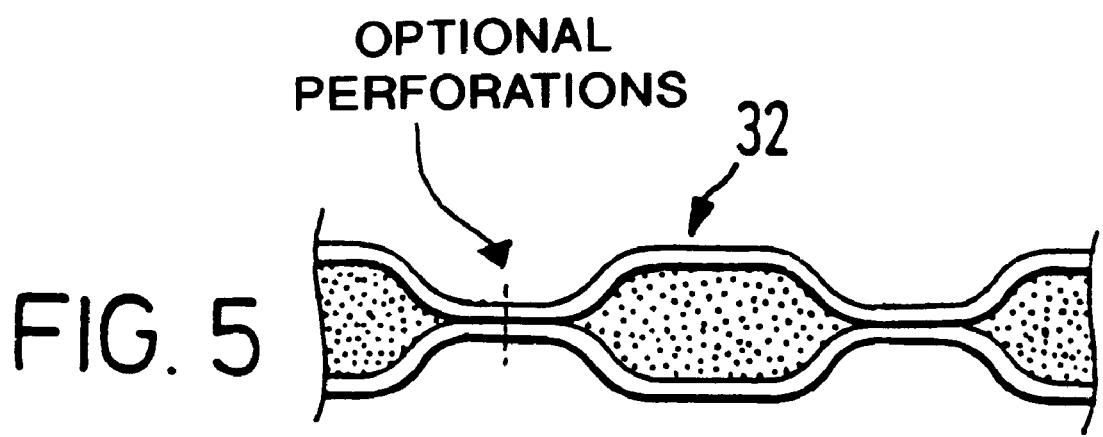
Figure 6:
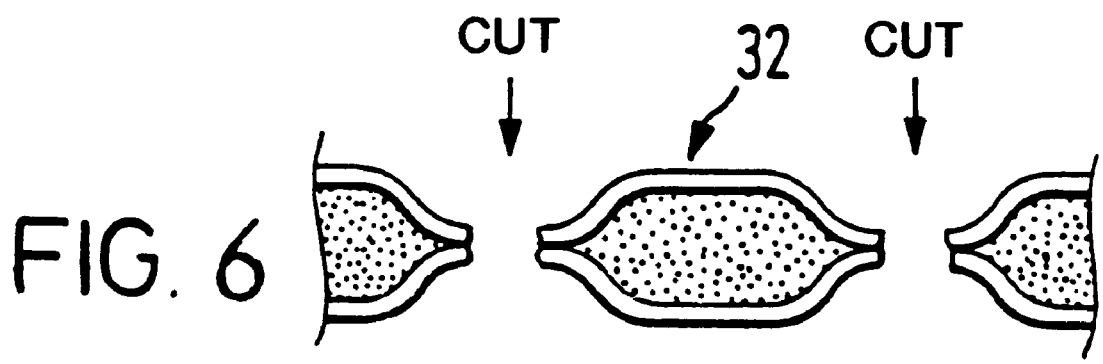

The laminate is then caused to take up a generally flat orientation, and passes to a sealing station where the sealing and cutting takes place, so producing packet-like articles. If desired the laminate may be left in a strip form as illustrated in FIG. 5 (i.e. without physically detaching the individual articles from each other). In such a strip, the articles may be divided by a weakened or perforated region so that an article may be torn off the strip later by a user. Alternatively, the individual articles may be separated as illustrated in FIG. 6.

The high-absorbency material can comprise absorbent gelling materials, such as superabsorbents. The absorbent gelling materials can be natural, synthetic and modified natural polymers and materials. In addition, or alternatively, the absorbent gelling materials can be inorganic materials, such as silica gels, or organic compounds such as cross-linked polymers; or alginates, reticular carboxymethylcelluloses, grafted starches, or synthetic derivatives of acrylamides or polyacrylates. Other high-absorbing materials which may be used are those specified in column 6 of U.S. Pat. No. 5,030,314.

A particular embodiment of the present invention will now be described with reference to the accompanying drawings, in which:

FIG. 1 is a diagrammatic side view of an apparatus for making packet-like articles for absorbing aqueous matter; and FIGS. 2–6 diagrammatically illustrate stages in the manufacture of packet-like articles.

EXAMPLE

A formulation comprising sodium polyacrylate 100 pbw, 0.5 to 6 pbw glycerol and 0.5 to 6 pbw water is mixed to a powder consistency in a conventional mixer 20 (see FIG. 1 of the accompanying drawings), and is fed onto a travelling sheet 21 of tissue paper which is pulled off a supply roll 22. A second (overhead) sheet 23 of tissue paper is fed from a second supply roll 24 and these two sheets sandwich the powder between them. The product passes between a first pair of rolls 26 which form a first nip 27 and to a second pair of rolls 28 forming a second nip 29. The inter-roll spacing at the second nip 29 may be for example 1.0 to 2.0 mm. That at the first nip 27 may be 0.75 to 4 mm. No external heat is applied. As described above, by employing specially-designed rolls, compressed zones are formed, and then loose superabsorbent powder located between these zones is removed, e.g. by suction or gravity. The resulting product may then be cut into suitable shapes, e.g. rectangles 32, by a conventional cutter 30, and, if desired, can be directly placed in an ostomy bag or incontinence pouch. It has been found to rapidly absorb a liquid such as urine. In tests of this product, at least 50 ml of synthetic urine was absorbed in under 60 seconds, usually under 40 seconds, by a product of one square centimetre area and 2 mm. in thickness.

Although the drawings illustrate production of the packet-like articles in a linear strip, it will be appreciated that the same principles may be used to produce a two-dimensional strip of such articles, for example, in a grid or other arrangement.

It will be appreciated that the foregoing description is merely illustrative of a preferred embodiment, and that many modifications may be made within the scope and principles of the invention.

I claim:

1. A method of making one or more articles capable of absorbing aqueous matter comprising:

a. arranging loose high-absorbent powder generally uniformly between upper and lower sheets;

b. compressing the powder and sheets in specific areas so as to structurally consolidate the powder in the compressed areas, while the powder in the surrounding areas remains loose; and c. extracting the loose powder.

2. The method according to claim 1, further comprising sealing the regions of the upper and lower sheets around the periphery of the consolidated areas to form sealed packet-like regions.

3. The method according to claim 1, further comprising cutting the regions around the consolidated areas.

4. The method according to claim 2, further comprising cutting the regions around the consolidated areas.

5. The method according to claim 1, in which the high-absorbent material includes at least one composition selected from the group comprising superabsorbents, absorbent gelling materials, natural, synthetic and modified natural polymer and silica gels.

6. The method according to claim 1, in which the high-absorbent material is an alkali metal polyacrylate.

7. The method according to claim 1, in which the high-absorbent material includes at least one composition selected from the group comprising alginates, reticular carboxymethylcelluloses, grafted starches and synthetic derivatives of acrylamides or polyacrylates.

8. The one or more articles capable of absorbing aqueous matter made pursuant to the method of claim 1.

* * * * *